(12) United States Patent
Leroy et al.

(10) Patent No.: US 9,388,095 B2
(45) Date of Patent: Jul. 12, 2016

(54) MULTISTAGE CRACKING AND STRIPPING PROCESS IN AN FCC UNIT

(75) Inventors: Patrick Leroy, Saint Vigor d'Ymonville (FR); Marc Bories, Saint Jouin de Bruneval (FR); Michaël Echard, Montivilliers (FR)

(73) Assignee: TOTAL RAFFINAGE MARKETING, Puteaux (FR)

( * ) Notice: Subject to any disclaimer, the term of this patent is extended or adjusted under 35 U.S.C. 154(b) by 474 days.

(21) Appl. No.: 13/877,788

(22) PCT Filed: Oct. 11, 2011

(86) PCT No.: PCT/FR2011/052366
§ 371 (c)(1),
(2), (4) Date: Jun. 17, 2013

(87) PCT Pub. No.: WO2012/049416
PCT Pub. Date: Apr. 19, 2012

(65) Prior Publication Data
US 2013/0267747 A1 Oct. 10, 2013

(30) Foreign Application Priority Data

Oct. 15, 2010 (FR) ...................... 10 58432

(51) Int. Cl.
*C07C 4/06* (2006.01)
*B01J 38/06* (2006.01)
(Continued)

(52) U.S. Cl.
CPC . *C07C 4/06* (2013.01); *B01J 38/06* (2013.01); *B01J 38/14* (2013.01); *C10G 11/18* (2013.01);
(Continued)

(58) Field of Classification Search
CPC .... C10G 11/18; C10G 11/182; C10G 51/026; C10G 2400/20; C10G 2300/1011; C10G 2300/301; C10G 2300/4081; C10G 2300/7093; C10G 2300/708; C10G 2300/807
See application file for complete search history.

(56) References Cited

U.S. PATENT DOCUMENTS 3,928,172 A 12/1975 Davis, Jr. et al.
5,702,589 A * 12/1997 Tsang .................... C10G 11/18
208/147

(Continued)

FOREIGN PATENT DOCUMENTS

EP 0 850 687 A2 7/1998
EP 1 577 368 A1 9/2005

(Continued)

OTHER PUBLICATIONS

Avelino Corma, et al., "Different process schemes for converting light straight run and fluid catalytic cracking naphthas in a FCC unit for maximum propylene production", Science Direct, Jul. 8, 2004, pp. 195-206, vol. 265, No. 2.

(Continued)

*Primary Examiner* — Prem C Singh
*Assistant Examiner* — Brandi M Doyle
(74) *Attorney, Agent, or Firm* — Sughrue Mion, PLLC (57) ABSTRACT

The present invention relates to a multi staged cracking and stripping process that can be used in a fluidized-bed catalytic cracking process or FCC (fluidized catalytic cracking) process for maximizing the production of olefins, that is to say of $C_3$ and $C_4$ olefins, in particular propylene and distillates.
One subject of the present invention is therefore a multi-staged process for cracking and stripping a fluidized mixture of hydrocarbons and of coked catalyst particles, integrated into a conventional fluidized-bed catalytic cracking process comprising at least one cracking step and one stripping step after separation of the particles of coked catalyst from the cracked effluent during the disengaging/stripping step, characterized in that it comprises at least two steps of cracking at least one hydrocarbonaceous fluid over the separated coked catalyst particles followed by at least two steps of stripping these particles, each cracking step preceding a stripping step. The present invention also relates to a separating and stripping device that implements this process.

18 Claims, 3 Drawing Sheets

(51) Int. Cl.
*C10G 11/18* (2006.01)
*C10G 51/02* (2006.01)
*B01J 38/14* (2006.01)

(52) U.S. Cl.
CPC ............ *C10G 11/182* (2013.01); *C10G 51/026* (2013.01); *C10G 2300/1011* (2013.01); *C10G 2300/301* (2013.01); *C10G 2300/4081* (2013.01); *C10G 2300/4093* (2013.01); *C10G 2300/708* (2013.01); *C10G 2300/807* (2013.01); *C10G 2400/20* (2013.01)

(56) References Cited

U.S. PATENT DOCUMENTS

| | | | | |
|---|---|---|---|---|
| 2004/0182746 | A1* | 9/2004 | Chen | ............ C07C 4/06 208/113 |
| 2005/0040075 | A1 | 2/2005 | Cerqueira et al. | |
| 2006/0021909 | A1 | 2/2006 | Cerqueira et al. | |
| 2009/0159497 | A1* | 6/2009 | Hedrick | ............ 208/67 |

FOREIGN PATENT DOCUMENTS

| | | |
|---|---|---|
| EP | 2 072 605 A1 | 6/2009 |
| EP | 2 113 299 A1 | 11/2009 |

OTHER PUBLICATIONS

International Search Report [PCT/ISA/210] dated May 14, 2012 in counterpart International Application PCT/FR2011/052366.

Japanese Office Action issued in corresponding Japanese Patent Application No. 2013-533260 issued Aug. 25, 2015.

* cited by examiner

MULTISTAGE CRACKING AND STRIPPING PROCESS IN AN FCC UNIT

CROSS REFERENCE TO RELATED APPLICATIONS

This application is a National Stage of International Application No. PCT/FR2011/052366 filed Oct. 11, 2011, claiming priority based on French Patent Application No. 10 58432, filed Oct. 15, 2010, the contents of all of which are incorporated herein by reference in their entirety.

The present invention relates to a multi-staged stripping process that can be used in a fluidized-bed catalytic cracking process or FCC (fluidized catalytic cracking) process for maximizing the production of olefins, that is to say of $C_3$ and $C_4$ olefins, in particular propylene. This process, which is integrated into the catalytic cracking process, participates in processes that limit the production of petrol, the production of which is over target especially in Europe, and therefore helps not only to increase the production of olefins but also to maximize the production of gas-oil bases. It applies to any FCC process comprising a step of reacting in a fluidized-bed riser or downer reactor, a step of separating and stripping the cracked hydrocarbons and coked catalyst particles and a step of regenerating the catalyst. It also relates to the devices for implementing said process, that can be used in a catalytic cracking unit, it being possible for the latter to comprise one or more riser and/or downer reactors.

The term "stripping" is understood here to mean the operation that consists in extracting the hydrocarbons trapped in the catalyst particles at the outlet of the fluidized reactor, using a gaseous fluid. Furthermore, the vessel of the FCC unit in which this operation is carried out is referred to as a disengager/stripper. Reference will also subsequently be made to the term "disengager" for the part of said disengager/stripper that makes it possible to separate the particles from the hydrocarbons by ballistic or centrifugal separation, and to the term "stripper" for the part of this disengager/stripper in which the stripping of the particles is carried out.

For many years, refiners and companies that hold licenses in FCC technologies have worked to optimise the operation of these processes and of the corresponding units. The optimisation of FCC processes was firstly directed towards the production of light products of the type of liquefied gases, naphthas and petrols, these products corresponding to the market demand. There was mainly a demand for light $C_2$ to $C_4$ olefins by polymer manufacturers and a demand for petrols mainly for the consumption of the light motor vehicle fleet, the demand for gas-oil bases not being predominant.

As a reminder, during a catalytic cracking operation, the feedstock is injected into a main reactor where it is brought into contact with hot catalyst particles in a fluidized bed, originating from the regenerator responsible for burning off, under an oxidising atmosphere, the coke deposited on the catalyst particles during the cracking of the feedstock. At the end of the reactor, the cracked hydrocarbons in gaseous form are separated from the coked catalyst particles in the disengager/stripper. At the outlet of the disengager of this disengager/stripper, the cracked hydrocarbons in gaseous form are sent to a fractionation unit in order to be divided therein into several hydrocarbonaceous fractions. Simultaneously, the coked catalyst particles are recovered in the stripper of the disengager/stripper in the form of a dense bed where they are flushed countercurrently with an inert gas, preferably steam, the role of which is to eliminate all traces of residual hydrocarbons trapped in the pores of each catalyst particle or in the interstices of the dense bed. At the outlet of the stripper, the coked and stripped catalyst particles are sent to the regenerator.

Generally, in stabilised operation, with no external stress, that is to say under stable conditions of temperature, pressure and circulation rate of the catalyst in the unit, a thermal equilibrium is obtained when the amount of coke formed remains constant in the reactor. This amount of coke formed and needed for the stability of the operation of the unit is characterized by the "delta coke". This delta coke corresponds to the difference between the amount of coke present at the inlet of the regeneration zone and that present on the regenerated catalyst at the outlet of this zone. If the delta coke and therefore the temperature of the regenerated catalyst increase due to the presence of hydrocarbons still trapped in the catalyst particles, it will be necessary to modify the parameters for regulating the unit. For example, it will be possible to reduce the throughput of the circulating catalyst particles in order to keep the reaction temperature of the feedstock to be cracked within acceptable limits or else to adjust the preheating of the feedstock.

Therefore, the engineers responsible for improving the operation of the FCC are particularly interested in the problem of the optimal stripping of the coked particles of catalysts recovered at the outlet of the reactor and of the possible configuration of the disengagers/strippers. Indeed, it is essential to separate the hydrocarbons trapped in the coked catalyst particles as efficiently as possible. An insufficient stripping of the coked particles is at the root of a higher combustion within the regenerator, therefore an increase in the production of heat transported by the catalyst into the reactor and finally an increase in unwanted dry gases and a loss of production of expected converted products such as $C_3$ to $C_4$ olefins, petrols and gas-oil bases. Moreover, overheating of the regenerator could cause metallurgical damage in extreme cases, and an accelerated deactivation of the catalyst. On the other hand, too long a stripping may be at the root of unwanted secondary reactions such as a particularly excessive coking of the catalyst particles that runs the risk of leading eventually to a partial deactivation of these particles. The stripping time should therefore be optimal in order to avoid these two pitfalls and to maintain stable operating conditions of the FCC unit.

The efficiency of the stripping operation is essential for the proper control of the cracking operations. This efficiency is measured by determining the residual hydrogen in the coke of the catalyst particles. A good stripping efficiency is referred to when this value is between 6 and 6.5% by weight relative to the weight of coke.

In order to achieve, or even improve, this stripping efficiency, the professionals of FCC processes have developed numerous technologies that make it possible to promote this separation. Generally, it has been proven that introducing baffles into the stripper in the path of the dense bed of catalyst particles towards the regenerator, while maintaining the countercurrent flushing of these particles with an inert gaseous fluid, promoted the desired separation.

At the same time as the implementation of these baffles, the professionals developed packings capable of better dividing the dense bed of coked catalyst particles into a multitude of streams and of making these particles more accessible to the stripping fluid and thus of further eliminating hydrocarbons trapped in the particles, for example in accordance with patent WO 01/047630.

The Applicant, in its patent EP 719 850, described a structured packing intended to be positioned in the stripper level with the formation of the dense bed of catalyst returning to the regenerator. This packing comprises at least one element, positioned over the entire cross section of the stripper at this level: this element comprises juxtaposed cells that orient substantially radially in order to divide the dense bed into a large number of streams, which thus allows the simultaneous passage of catalyst particles and of stripping fluid. More specifically, the Applicant recommended the use of folded sheets positioned on one another so that the respective folds of two sheets placed side by side make an angle that varies from 10 to 90°.

Since then other packings have been proposed. For example, in patents U.S. Pat. No. 7,022,221, U.S. Pat. No. 7,077,997 and WO 2007/094771, deflectors are proposed that are in the form of plates positioned in the stripper around the riser, each plate comprising a multitude of orifices determined by gratings or holes formed that have walls which are sloped relative to the plane of said plate. These orifices let through the particles and the stripping gas injected countercurrently relative to the stream of catalyst particles from at least one point located downstream of the deflectors.

In patent WO 00/35575, the intersection of pairs of small plates having planar metal sections is proposed in order to create a packing for the stripper part of the FCC in order to divide the stream of coked catalyst as above with a gaseous stream being sent countercurrently which is injected downstream of this intersection.

In the published Chinese patent CN 1763150, several plates comprising a regular arrangement of guide blades perpendicular to the plane of each of the plates are positioned in the stripper one on top of the other. The adjacent plates are placed so that the blades of the first are perpendicular to those of the second and so on so as to determine preferential paths that enable the division and stripping of the catalyst particles by the stripping fluid injected downstream of the plates countercurrently.

In patent EP 1 577 368, it is a question of integrating around the riser, inside the stripper, a packing constituted of several superposed layers, each of them being constituted of a plurality of juxtaposed corrugated ribbons. Preferably, two adjacent layers are positioned so that the ribbons of the first layer and those of the second layer make a non-zero angle. The peaks, valleys and orifices of one plate taken in combination with the peaks, valleys and orifices of the plates positioned on either side define a path in the thus structured packing that allows the circulation of the stream of catalyst particles and the stripping thereof by a stripping fluid injected downstream of said packing.

In all these packings, the objective is to optimise the stripping of the catalyst but none constitutes a means of reducing the production of unwanted hydrocarbons, which is the objective of the present invention.

Within a context of maximizing the production of light olefins and of minimising petrols produced in FCC, the Applicant proposes to recycle the unwanted hydrocarbons recovered at fractionation to the FCC stripper in order to crack the latter.

Despite the reduction in the catalytic activity of the solid which is linked to the presence of coke, Professor Corma has demonstrated (Corma et al., Applied Catalysis A: General 265 (2004) 195-206) that the degree of conversion of a light hydrocarbonaceous fraction, for example a catalytic petrol, in a dense bed under cracking conditions such as those encountered in a stripper has proved to be advantageous with, in particular, the production of propylene ($C_3$ olefin) with little coke and dry gases.

This technology has already been envisaged by patent U.S. Pat. No. 7,658,837, which proposes the homogeneous injection of one or more hydrocarbon streams, for example streams of naphtha or of LCO (light cycle oil) of FCC origin or from a coker, making it possible either to reduce the sulphur and to improve the quality of the products or to promote the production of light olefins, in particular of propylene type.

The use of this type of recycle, but with hydrocarbons being able to produce more coke, has also been described in document EP2072605 for increasing the amount of coke on the catalyst sent to the regenerator, the purpose of this addition of coke being the operation of the regenerator as a gazificator, susceptible to produce synthesis gas, by not injecting oxygen into the regenerator but a mixture of oxygen, steam and carbonic gas ($CO_2$), coming from other neighbouring unities.

In these two documents, the hydrocarbons are cracked in a single step in the striper, striping steam being injected after the cracking step, but also before in document EP2072605.

The objective of the present invention is to transform the step of an FCC process, used exclusively for separating and stripping the catalyst particles and limiting the entrainment of hydrocarbons to the regenerator, to at least two reaction (cracking) steps and at least two stripping steps that makes it possible to improve the economic performances of the FCC process without modifying the efficiency of the stripping which is the initial function of such a step.

The Applicant has therefore developed a novel reaction and stripping process which combines the multi-cracking of hydrocarbons over the coked catalyst particles, in particular hydrocarbons whose production it is desired to minimise, and the stripping of these coked catalyst particles in the presence of a particular packing, especially in the stripper where this stripping takes place. It is a question here of using the thus modified stripper as a new cracking multi-zone, that is with several cracking steps, in which it is possible, for example, to recycle unwanted hydrocarbons the production of which it is desired to reduce, obtained by cracking in the main reactor. The Applicant envisages this combination both for remodeling existing units and for constructing new units.

The present invention aims to increase the operational flexibility of FCC units as a function of the markets. This flexibility is achieved by minimising the production of unwanted hydrocarbons and by maximising the production of high value-added hydrocarbons such as light $C_3$ and $C_4$ olefins and/or distillates of gas-oil type via the implementation of a novel multi-staged reaction and stripping process that can be easily integrated into a conventional catalytic cracking process.

The expression "conventional cracking process" is understood here to mean a process that comprises a step of reacting a hydrocarbonaceous feedstock over a fluidized bed of ascending or descending catalyst, a step of disengaging/stripping the coked catalyst particles from the cracked effluents (that is to say separating the particles from the effluents, then stripping of these particles), and finally a step of regenerating, in one or more stages, the coked catalyst particles, the regenerated catalyst particles recovered at the outlet being sent to the inlet of the fluidized bed of the reaction step.

One subject of the present invention is therefore a multi-staged process for cracking and stripping a fluidized mixture of hydrocarbons and of coked catalyst particles, integrated into a disengaging/stripping step of a conventional fluidized-bed catalytic cracking process, said multi-staged process comprising at least one step of cracking and one step of stripping after separation of the coked catalyst particles and of the cracked effluents, characterized in that said multi-staged process for cracking and stripping comprises at least two steps of cracking at least one hydrocarbonaceous fluid over the separated coked catalyst particles followed by at least two steps of stripping these particles, each cracking step preceding a stripping step.

Within the context of the present invention, the hydrocarbonaceous fluid is injected over the coked catalyst particles by means of one or more injectors during each cracking step, whilst the coked catalyst particles are stripped during each stripping step, by a stripping fluid, injected countercurrently to the catalyst particles used in the preceding step.

Among the advantages of the invention, the first advantage is to create at least two supplementary reaction zones in addition to the riser or downer reactor(s) in the same FCC unit: it makes it possible to consume hydrocarbons whose production it is desired to limit, without limiting the hydraulic capacity of the unit, and while ensuring an efficient stripping of the catalyst at the outlet of the stripper in order to maintain the thermal equilibria of the FCC unit.

In one preferred embodiment of the invention, the process according to the invention, integrated into the disengaging/stripping step of a conventional catalytic cracking unit, will advantageously comprise upstream of the first cracking step, a step of pre-stripping the catalyst that consists in countercurrently flushing the stream of coked catalyst particles (resulting from the cracked effluents/coked catalyst separation) with a stripping fluid injected countercurrently to said stream; the throughput of this fluid preferably varies from 10 to 40% of the total throughput of fluid used for the stripping of the coked particles in said process according to the invention.

The addition of a phase of pre-stripping the catalyst particles constitutes the second advantage of the invention: this phase makes it possible to restore a portion of the activity of the catalyst by eliminating (at least partially) the hydrocarbons that are left trapped and adsorbed in the particles after separation, before the first the cracking step, and therefore to maximise the conversion of the hydrocarbonaceous fraction injected during the first cracking step.

Preferably, the particles are distributed into the various compartments dedicated to the cracking and optionally to the stripping by means of at least one structured packing element described, in particular, in the patents cited in the present description.

These structured packing elements allow a completely homogeneous distribution of the solid particles over the entire section of the stripper. The flow of the solid is then similar to plug flow without backmixing, improving the contact between the solid and gaseous phases without preferential passage of the gas. Furthermore, the rising gas bubbles, the volume of which has a tendency to increase via coalescence of smaller bubbles, are then broken up during passage into such structured packings, which promotes the transfer of material between the gas phase and the solid phase.

In the absence of such packing elements, the volume of the gas bubbles would thus limit their residence time in the stripper due to their excessively high upward velocity. The exchange of material with the downward solid would then be greatly limited due to the short residence time of the bubbles in the stripper but also due to the reduction of the exchange area between the two phases, the bubbles being too large.

Furthermore, the cracking conditions, in the catalytic sense of the word, are very favourable, with an extremely high catalyst to hydrocarbons ratio (C/O), comprised between 30 and 200, and a reaction temperature slightly below that measured at the outlet of the reactor in the region of 1 to 5° C.

One advantage of the present invention is also that it makes it possible to create optimal hydraulic, catalytic and thermal conditions for limiting the production of coke and of dry gases in favour of light ($C_3$ to $C_4$) olefins even though the activity of the catalyst used is reduced by the residual coke present. This drop in catalytic activity is largely compensated for by the very high catalyst to hydrocarbons ratio.

This pre-stripping step is quite similar to that carried out by a person skilled in the art via the use of structured packing elements for stripping hydrocarbons still present in the catalyst particles before the regeneration step.

The stripping steps of said process according to the invention comprise(s) at least one injection of gas constituted predominantly, for example at least 60% (volume), of steam.

The cracking step(s) comprise(s) at least one injection of hydrocarbons, preferably a recycled hydrocarbonaceous fraction, which may contain less than 5% (volume) steam, in particular to help in the atomisation and vaporisation of the heaviest hydrocarbons, especially distillates of gas-oil type. For example, the injected hydrocarbonaceous fraction with advantageously comprise from 1 to 3% (volume) of steam.

Another technical effect of the invention is to obtain a more selective cracking during the cracking steps for maximising the production of a desired product during the disengaging/stripping step. Comparatively to the cracking in the main reactor, the cracking in the disengaging/stripping step is performed in conditions such that the ratio of flow of catalyst over the flow of fresh feed (C/O) is high and the temperature lower, which promotes the catalytic reactions compared to the thermic reactions, these last generating non desired products, as dry gases. Then, the use of hydrocarbon recycles in the striper allows the reduction of the severity of cracking conditions in the main reactor (typically by lowering the reaction temperature). Thus, the cracking of a catalytic petrol in a dense fluidized bed results selectively in the production of liquefied petroleum gas or LPG, which will make it possible, at the same total production of LPG, to lower the reaction temperature (TRX or ROT) of the main reactor for cracking the feedstock. By reducing this temperature, the production of dry gases and other secondary products such as diolefins will be reduced, thus relieving the cracked gas compressor positioned at the top of the column for fractionating the cracked effluents. This volume saving could be benefited from by further cracking petrols in the stripper and/or by using more ZSM5-type conversion additive, in order to increase the production of LPG both in the main feedstock cracking zone and in the cracking steps of the stripping zone.

Another technical effect of the present invention is to be able to benefit from a cat cooler (or cooling of the catalyst) effect independent of the ROT or TRX. If the production of coke remains low, the hydrocarbonaceous fraction introduced downstream of a cracking phase will cool the catalyst particles. For example, for a unit for which the circulation throughput is 40 tonnes/minute (t/min), the introduction of 20 tonnes/hour (t/h) of petrol during a cracking step will result in the temperature of the catalyst particles being decreased by 5° C., this decrease in temperature also being observed in the dense phase of the catalyst present in the regenerator.

In the process according to the invention, two cracking steps that is inserted between two stripping steps therefore promote the conversion of a hydrocarbonaceous fraction having a boiling point typically below 220° C. into light hydrocarbons of the GPL type, without modifying the hydraulic equilibrium of the catalytic cracking process in which it is integrated, by slightly increasing the amount of coke present on the catalyst particles.

In an FCC process operating in the mode for maximising distillates, especially of gas-oil type, the recycle would advantageously comprise the petrol produced or any fluid having a boiling point less than or equal to 220° C. or else products of HCO (heavy cycle oil) type or slurries (residual hydrocarbonaceous slurries) recovered at the hydrocarbon fractionating step of the FCC process. In this mode for maximising distillates, it will be preferred to work at low conversion with a reaction temperature in the main reactor varying typically from 490° C. to 510° C., which corresponds to ratios of the flow of catalyst over the flow of fresh feed (C/O) varying from 4 to 6.

It is also possible to introduce into the process of the invention hydrocarbons originating from other refining units (coker, hydrocracker, visbreakers, atmospheric distillation, etc.) or even products resulting from biomass, for example plant oils or green hydrocarbons resulting from first or second generation biomass. It would not be outside the scope of the invention if hydrocarbons were introduced simultaneously in combination with plant oils such as rapeseed oil or palm oil. In one preferred embodiment of the invention, the hydrocarbons for the recycle may be chosen from $C_6$ and $C_7$ olefins and oligomers having a boiling point of less than 220° C. resulting from the polymerisation of $C_2$ to $C_5$ olefins.

The various hydrocarbons described above may be introduced individually or as a mixture.

Thus, it is possible to inject hydrocarbons of the same nature into different cracking steps or hydrocarbons of different nature at each of the cracking steps or else hydrocarbons of different nature jointly into one and the same cracking step.

Preferably, in order to achieve the common objective of maximizing the distillates and of optimizing the production of $C_3$ and $C_4$ olefins, and more particularly propylene, injected into the first cracking step is at least one hydrocarbon chosen from the petrol produced or any fluid having a boiling point less than or equal to 220° C., preferably less than or equal to 160° C. and injected into the second cracking step are products of HCO type or slurry, recovered at the hydrocarbon fractionating step of the fluidized-bed catalytic cracking process, these two steps being separated by a stripping step.

In such a configuration, the ROT or TRX will preferably be chosen to be between 490 and 510° C., resulting from a ratio of the flow of catalyst over the flow of fresh feed (C/O) comprised between 4 and 6 allowing the minimization of the conversion in the main reactor, typically comprised between 60-65% wt.

In another preferred embodiment, the process according to the invention will comprise a sequence of cracking and stripping steps, optionally comprising an initial pre-stripping step. It is possible to introduce as many cracking and stripping steps as are desired, the last step always being a stripping step in view of preparing the catalyst particles to be regenerated, this step reducing the entrainment of hydrocarbons capable of increasing the temperature of the regenerator.

A stripping step will advantageously comprise at least one structured packing element and a system for injecting steam countercurrently to the catalyst stream. In the same way, a cracking step will comprise a system for injecting hydrocarbons and optionally at least one structured packing element in all or part of the volume dedicated to cracking.

The arrangement and the operating conditions of the process of the invention will be adjusted so as to meet the rules commonly applied by those skilled in the art, in particular the upward velocity of the gases, the downward solid stream and the residence time in particular at the stripping step before re-entry of the catalyst into the regenerator.

In the catalytic cracking process that integrates the process of the invention, the catalyst is a conventional catalyst dedicated to the production of petrol from heavy feedstock of atmospheric residue type (total surface area preferably greater than or equal to $110\,m^2/g$, and for which the content of contaminating metals, nickel and vanadium, is preferably less than 10 000 ppm by weight in order to limit the undesirable secondary effects such as the production of dry gases (that is to say, in particular, the production of ethylene, methane, hydrogen and $H_2S$) and coke. In one preferred embodiment of the invention, it is possible to add to the catalytic mass constituted by this conventional catalyst completely or partly coked in certain phases of the process, up to 15% by weight of additive, for example of ZSM5 additive, which promotes the formation of olefins by cracking of petrols, whether they result from the cracking of the feedstock injected into the riser reactor or from the hydrocarbon recycle in the stripper of the disengager/stripper of the catalytic cracking unit. In practice, above the concentration of 15% by weight of additive, a phenomenon of dilution of the catalytic activity of the catalyst carrying out the cracking of the feedstock is observed, which limits the production of petrol molecules and consequently the production of light C2 to C4 olefins. The additive make-up may be carried out independently of the catalyst make-up, as a mixture with the latter in the appropriate ratio.

Another subject of the present invention is a cracking and stripping device suitable for catalytic cracking units that is placed in the stripper of the disengager/stripper (7) positioned downstream of the main reactor containing the fluidized bed, this vessel comprising a disengager for the centrifugal and/or ballistic separation of the catalyst particles and of the cracked hydrocarbons resulting from the main reactor, and a stripper (9) for stripping the catalyst particles which is positioned upstream of the outlet (8) of the catalyst to the regenerator, characterized in that the stripper comprises at least four compartments, including at least two cracking compartments (2) and at least two stripping compartments (3), eventually equipped with structured packing elements, these elements occupying all or part of the section of said compartment, and each compartment comprising, at its base, at least one means (5) of injecting gaseous fluids, for example by means of an injection ring and/or injectors.

In one preferred embodiment of the invention, the device comprises, in addition, at least one pre-stripping compartment (1) for pre-stripping the catalyst particles that is located upstream of the cracking compartment (2), advantageously equipped with at least one injector (3) for injecting stripping fluid and optionally with at least one structured or non-structured packing.

Preferably, the device of the invention comprises a plurality of intercalated cracking and stripping compartments, equipped with at least one means of injecting gaseous fluids, the volumes of all of the cracking and stripping steps corresponding respectively to 25 to 65% and 35 to 75% of the total volume occupied. If there is a pre-stripping compartment, this could occupy up to 25% of the volume dedicated to the stripping.

According to the invention, the cracking and stripping compartments are equipped with structured packing elements as described above in the patents cited in the present description. More particularly, in the cracking compartments of the device according to the invention, the packing elements will occupy all or part of the section of the compartment. Thus it would not be outside the scope of the present invention if over the entire height of a cracking compartment, this compartment was cut into at least two sections, one being equipped with a packing, the other remaining free and/or equipped with baffles. Such a configuration enables the cracking of different hydrocarbons in two different sections of the same compartment.

For injecting gaseous fluids or vaporisable liquid hydrocarbons into the stripping and/or cracking compartments, the means for injecting gaseous fluids are preferably chosen from spraying rod-type injectors and dispersion rings.

For a better understanding of the invention, the appended drawings schematically show the stripping devices of the prior art compared with devices of the invention, these being given by way of non-limiting illustration of the invention.

Embodiment A is a conventional FCC unit, for which the stripper of the disengager/stripper is equipped with internals known as "disc and donuts": this technology displays hydraulic limitations when the stream of catalyst becomes too large or obstruction phenomena, similar to what may be encountered in distillation columns.

Embodiment B describes, like A, the stripper of the disengager/stripper but in which structured elements of the technology described in the patents cited in the present description have been introduced: in a conventional arrangement, these internals make it possible to operate at very high catalyst flows while retaining a very good stripping efficiency. Each compartment comprises at least one structured element or packing and a ring for distributing gas that is placed downstream of the packing.

Embodiment C is a device according to the invention positioned within the stripper of the disengager/stripper.

Figure 1:
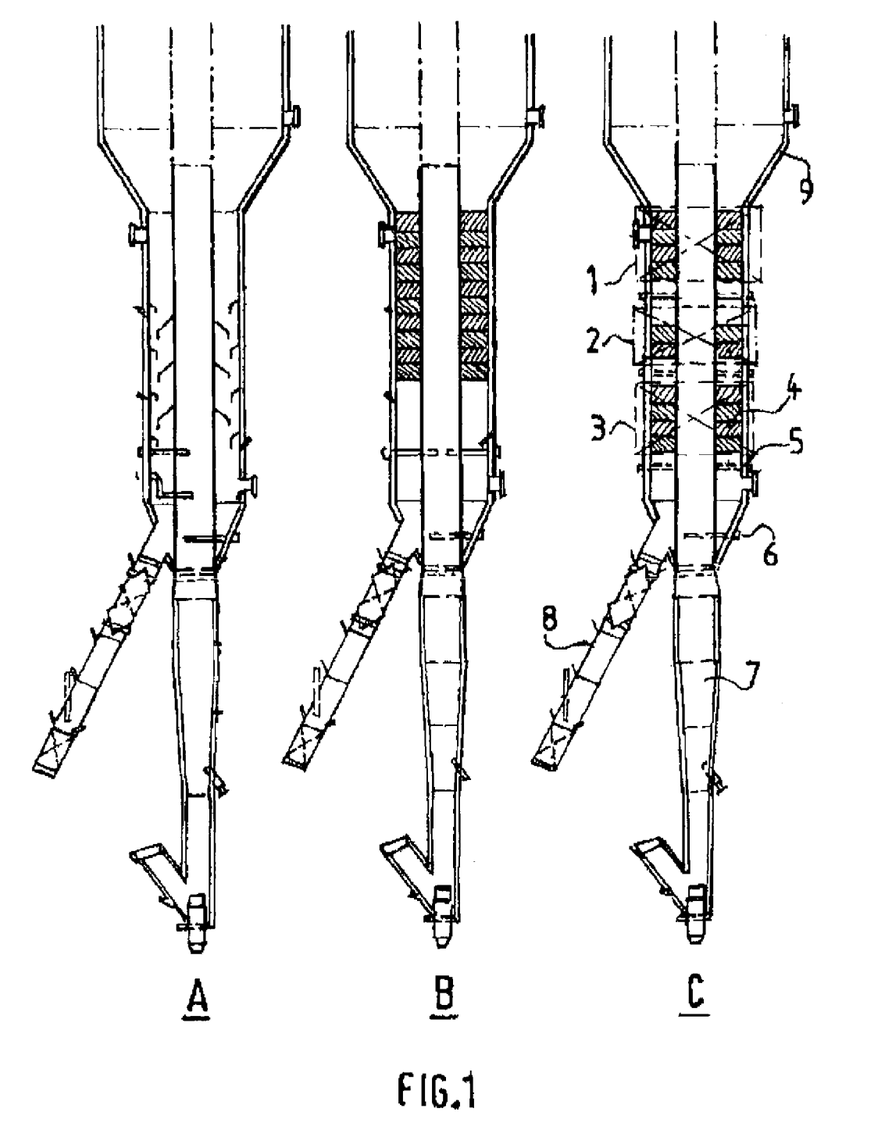
FIG. 1 comprises three embodiments of a disengager/stripper for the coked catalyst/cracking effluents from the main reactor separation and for the stripping, embodiments A, B and C.

In FIG. 1, embodiment C features the stripper of the disengager/stripper which contains several compartments. Each compartment has a different functionality. Here there are 3 compartments (1), (2) and (3) represented in the same stripper. The first compartment (1), referred to as the pre-stripping compartment, makes it possible to partially or completely eliminate the hydrocarbons trapped in the catalyst at the outlet of the disengager, a cracking compartment (2) into which a hydrocarbonaceous fraction is injected, and a final stripping compartment (3) necessary for extracting the hydrocarbons trapped in the catalyst before the regeneration of this catalyst in air in the regenerator of the FCC unit.

It is possible to introduce as many compartments as desired into the same stripper as long as the last compartment of such an arrangement is that of the final stripping, with steam or another inert gas, of the catalyst with a view to preparing it for its regeneration by reducing the entrainment of hydrocarbons capable of increasing the temperature of the regenerator.

Figure 2:
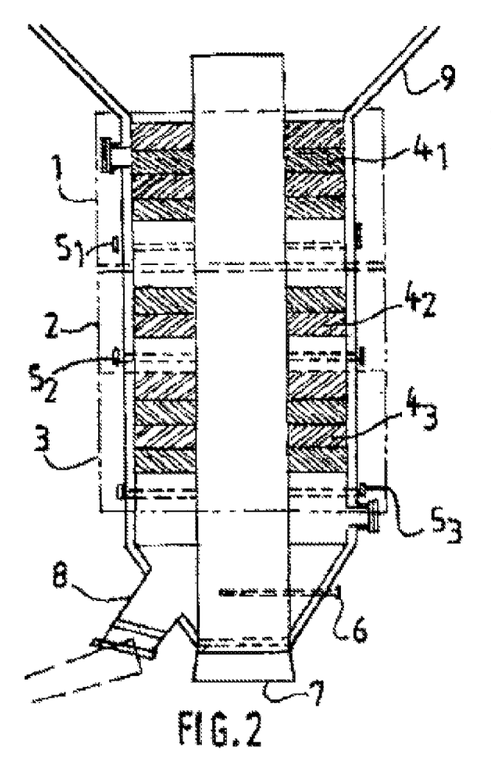
FIG. 2 shows details of an embodiment of C according to the invention.

In FIG. 2, the device according to the invention is described and comprises three compartments (1), (2) and (3) positioned around the riser reactor (7) in the stripper (9) of a disengager/stripper of a conventional FCC unit, before the catalyst (8) is discharged to the regenerator. Compartment (1) is a pre-stripping compartment, comprising a structured packing ($4_1$) that comprises one or more packing stages and an injection of steam ($5_1$). Compartment (2) is a cracking compartment, comprising a structured packing ($4_2$) that comprises one or more packing stages and an injection of hydrocarbons ($5_2$). Compartment (3) is a stripping compartment, comprising a structured packing ($4_3$) that comprises one or more packing stages and an injection of steam ($5_3$).

Figure 3:
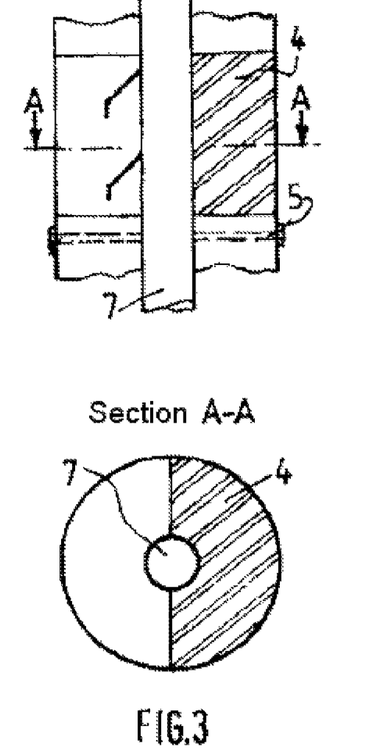
FIGS. 3 and 4 show details of a cracking compartment in which only a portion of the cracking space is filled with structured packing.
Figure 4:
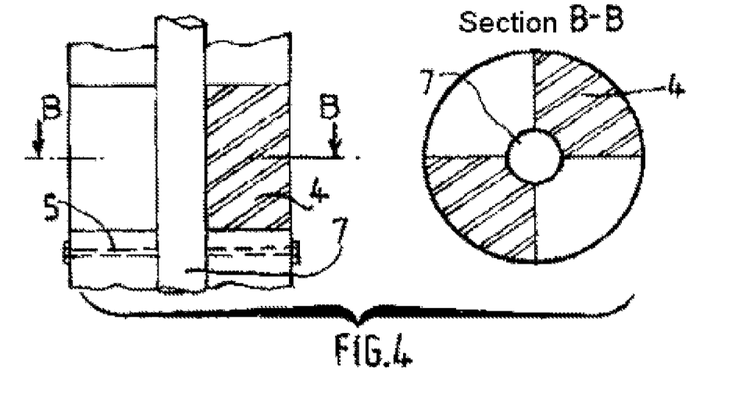

In FIGS. (3) and (4), a cracking compartment is described in which the packing (4) only occupies a portion of the compartment. In FIG. (3), the structured packing (4) only occupies half of the compartment over the entire height thereof. In FIG. (4), it can be seen that the packing (4) occupies two non-neighbouring quarters over the entire height of the cracking compartment.

Figure 5A:
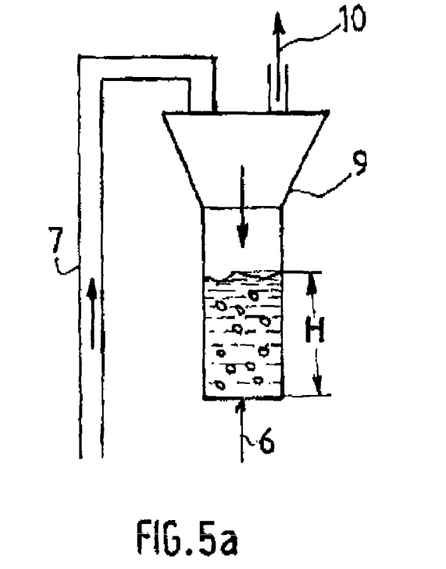
FIGS. 5a, 5b and 5c describe the various modifications made to the stripper of the disengager/stripper of a catalytic cracking pilot plant supporting the demonstration of Example II below.
Figure 5B:
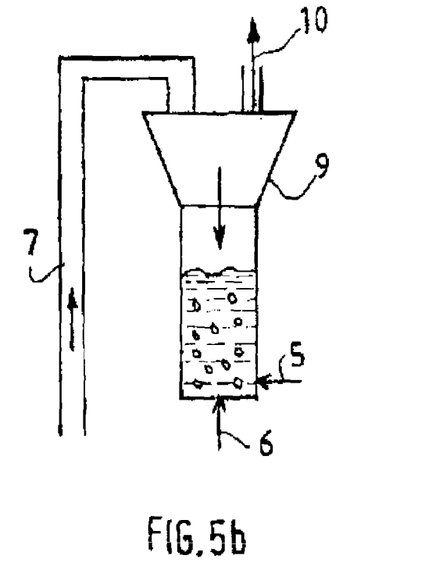
Figure 5C:
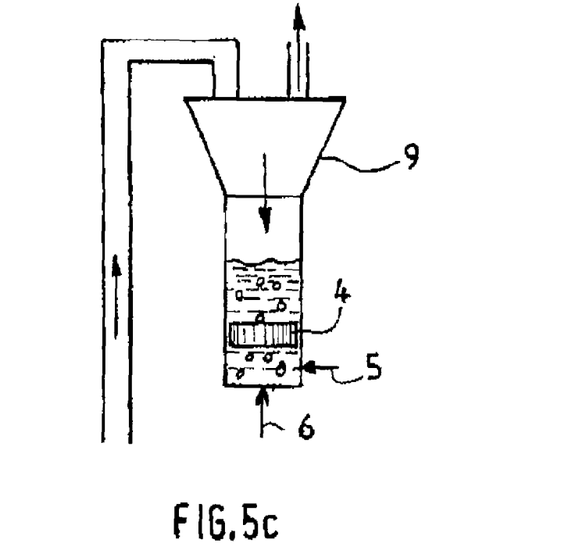

FIGS. 5(a), 5(b) and 5(c) simulate the stripper in the disengager/stripper of a catalytic cracking unit: the stripper is represented without recycle in FIG. 5(a), with hydrocarbon recycle (5) in FIG. 5(b), and with hydrocarbon recycle (5) and introduction of a packing element (4) in FIG. 5(c).

In all of the figures, the same references denote the same components.

The examples below aim to illustrate the effects of the invention and its advantages, but without limiting the scope thereof.

EXAMPLE I

The present example aims to reproduce, via pilot tests, what takes place in a fluidized-bed cracking reactor with a view to demonstrating the advantage of pre-stripping the coked catalyst with a non-zero content of residual carbon, with a view to restoring a portion of its activity before a new cracking step as claimed within the context of the present invention.

A catalyst referenced A (Conquest 85 from Albermarle) used conventionally, after regeneration, is introduced into a catalytic cracking pilot plant. This is an ACE-Model R+ (Advanced Cracking Evaluation-research unit with automatic catalyst addition) pilot plant sold by Kayser Technology. This is a tool that enables the selective testing of fluidized-bed catalytic cracking catalysts, the evaluation of feedstocks and the technical monitoring of the performances of the industrial units.

This regenerated catalyst with a zero content of residual carbon undergoes a catalytic cracking operation in a fluidized-bed FCC pilot plant. A conventional feedstock of highly paraffinic vacuum distillate (VD) type is injected into the fluidized bed at a reaction temperature of 520° C., the cracking conditions are such that the catalyst to feedstock weight ratio (R) is 5. A first cracking of the feedstock is carried out over the regenerated catalyst A, a second cracking is carried out when the catalyst used is that recovered after the first cracking step; it will be given the reference B. At the end of this second cracking step, the catalyst B is stripped in order to give catalyst C which will be used in a third cracking step for cracking the same feedstock.

All the results are collated in Table I below: the first column gives the yields obtained for the first cracking of the feedstock over the completely regenerated catalyst A, the second column gives the yields obtained with catalyst B (catalyst A coked during the first cracking) and the third column gives these yields with catalyst C (catalyst A coked during the first cracking and that has undergone prior stripping).

TABLE I

|        | Catalyst A | Catalyst B | Catalyst C |
|--------|------------|------------|------------|
| H2-C2  | 1.26       | 1.34       | 1.01       |
| C3=    | 4.90       | 2.10       | 4.14       |
| C3(all)| 5.78       | 2.50       | 4.79       |
| iC4    | 3.71       | 0.73       | 1.81       |
| nC4    | 0.71       | 0.21       | 0.42       |
| iC4=   | 1.75       | 1.03       | 1.81       |
| C4 (all)| 10.17     | 3.67       | 7.05       |

TABLE I-continued

|  | Catalyst A | Catalyst B | Catalyst C |
|---|---|---|---|
| LPG | 15.95 | 6.17 | 11.85 |
| PI-160° C. | 34.94 | 15.58 | 27.65 |
| 160-221° C. | 11.57 | 7.03 | 9.59 |
| Petrol C5-221° C. | 46.51 | 22.62 | 37.25 |
| LCO 221-360° C. | 11.07 | 14.92 | 11.95 |
| Bottom residue 360+ | 22.72 | 54.64 | 36.16 |
| Coke | 2.49 | 0.40 | 1.78 |
| Delta Coke | 0.50 | 0.08 | 0.36 |
| Conversion - 221° C. | 66.21 | 30.43 | 51.89 |
| Liquid conversion* | 73.53 | 43.71 | 61.04 |
| R | 5.00 | 5.00 | 5.00 |

*liquid conversion = LPG + petrol + LCO

It is observed that the standard conversion changes from close to 44% for the unstripped coked catalyst (B) to 61% for the coked but stripped catalyst (C). However, it remains below the liquid conversion level achieved by the completely regenerated catalyst (A), here 73.5%. The elimination of the residual hydrocarbons present in the interstices of the catalyst or else in the inter-particle spaces therefore made it possible to significantly restore the catalytic activity of the catalyst (C) or (A coked then stripped).

The results of these tests clearly show the advantage of stripping the catalyst after a first cracking step in view of its use for a new cracking step, even if the latter has a high residual content of carbon or coke, here 0.5%.

EXAMPLE 2

The present example aims to demonstrate the advantage that exists in using a packing-type internal with a view to increasing the cracking in the disengager/stripper of a fluidized bed when a hydrocarbon is recycled in the presence of said internal, said internal improving the contact between the gas phase and the fluidized solid.

Tests were carried out on a continuous and adiabatic fluidized pilot plant, representative of an industrial catalytic cracking unit. This pilot plant is equipped with the same equipment as an industrial unit. This unit comprises a riser, at the bottom of which the feedstock to be cracked is injected, a disengager/stripper for firstly separating the cracked gases from the catalyst then for stripping the coked catalyst, a regenerator for burning off the coke present on the catalyst arriving at the disengager/stripper with a view to restoring the activity thereof before its return to the lower end of the riser. The regeneration step may be carried out in one or two steps.

The disengager/stripper, represented in FIG. 5a, was modified to allow the recycle of a hydrocarbon (reference 5 in FIGS. 5b and 5c) and the cracking thereof over stripped or unstripped coked catalyst, with a view to assessing its crackability under various conditions. FIGS. 5a, 5b and 5c comprise a riser reactor (7) connected in its upper part to a disengager/stripper (9), comprising in its upper end a conical part for receiving the coked catalyst and a discharge pipe (10) for discharging the cracking effluents of the feedstock injected into the reactor, and in its lower end a cylindrical part containing the bed of coked catalyst having a height H, comprising a gas injector (6) for stripping the coked catalyst particles which will be sent to the regenerator. In FIG. 5b, a petrol injector (5) has been added for the recycle of petrol to the coked catalyst bed: in FIG. 5c, a packing element (4) was added above the petrol injection (5) in order to improve the petrol/coked catalyst contact.

The operating conditions are the following:
throughput of fresh feedstock injected at the bottom of the riser reactor (7)=5.5 kg/h
preheating temperature of the fresh feedstock=200° C.
reaction temperature at the top of the riser=510° C.
throughput of air adjusted for the regenerator in order to obtain an excess of $O_2$ of 2 vol %
throughput of stripping nitrogen=450 Nl/h without injection of petrol and 400 Nl/h in the presence of petrol (5) injected at the bottom of the disengager/stripper
the catalyst feed is adjusted to balance the heat balance. For all our tests, it is kept constant and in the vicinity of 45 kg/h
throughput of injection of petrol (5) in the bottom of the disengager/stripper=1 l/h
there is only a single packing element to promote the contact between the gas (6)+(5) rising in the stripper and the descending solid.

The catalyst used is identical to the catalyst used in Example I. Its catalytic activity MAT was measured at 67% for an active surface area of 125 $m^2/g$. This catalyst does not comprise an LPG booster additive based on ZSM5.

The fresh feedstock injected at the bottom of the reactor (7) is a vacuum distillate previously of a distillation fraction having a temperature between 350 and 550° C. The petrol recycled into the stripper in liquid form is a catalytic petrol, referred to as heart cut petrol, having a boiling range between 90 and 160° C. for a density at 15° C. of 752 $kg/m^3$.

Several tests were carried out in the configurations from FIGS. 5b and 5c and the results have been collated in Table II below. During these tests, the material balances are obtained between 97 and 102%.

TABLE II

| Configuration | 5b | 5c |
|---|---|---|
| Recycled product | Heart cut petrol | Heart cut petrol |
| H2 | 0.25 | 0.21 |
| C1 | 1.38 | 1.25 |
| H2S | 0.01 | 0.01 |
| C2 | 1.53 | 1.41 |
| C2= | 0.94 | 0.84 |
| Dry gases H2-C2 | 4.11 | 3.72 |
| C3 | 2.02 | 1.50 |
| C3= | 2.65 | 6.50 |
| iC4 | 0.16 | 2.40 |
| nC4 | 0.90 | 0.55 |
| C4$^{=1}$ | 0.45 | 0.56 |
| iC4= | 1.81 | 3.10 |
| C4$^{=2}$ | 0.36 | 1.58 |
| LPG | 8.34 | 16.19 |
| LCN (Pi-100° C.) | 14.69 | 16.7 |
| MCN (100-150° C.) | 42.84 | 3747 |
| HCN (150-220° C.) | 13.03 | 11.2 |
| TCN (i-220° C.) | 70.55 | 65.37 |
| LCO (220-350° C.) | 8.49 | 7.24 |
| DCO (350+° C.) | 6.91 | 5.41 |
| Coke | 1.60 | 2.07 |

The crackability of the recycled petrol is estimated by taking the differences between the material balances, averaged beforehand, achieved without recycle and with recycle.

In the absence of packing element (configuration 5b), the cracking level of the recycled petrol remains relatively low with a limited production of LPG. The introduction of a single packing element (configuration 5c) makes it possible to significantly increase the production of LPG and more particularly that of propylene (C3=).

Thus, in the configuration (5b), the petrol injected in liquid form vaporises rapidly forming large bubbles which rise very rapidly in the bed, which very greatly limits the transfer of material between the two phases (catalyst/vaporised liquid). The use of a packing element (configuration 5C) makes it possible, on the one hand, to reduce the size of the bubbles but "forces" the latter to come into contact with the descending solid, the catalyst/vaporised liquid contact thus being greater.

EXAMPLE 3

The present example aims to demonstrate the impact of recycling the light petrol and the HCO produced in the riser to the stripper for the purpose of maximizing the production of distillate while maintaining the production of LPG.

The data presented is derived from results obtained in the laboratory on a circulating-bed adiabatic pilot plant similar to an industrial plant on a feedstock composed predominantly of atmospheric residue and a catalyst of moderate activity (MAT~65). The results are given in Table III below for the various steps envisaged.

TABLE III

| Configuration | Case 1 | Case 2 | Case 3 |
|---|---|---|---|
| Mode | Petrol | Distillate | Distillate |
| Recycle stripper | No | No | YES (LCN and HCO) |
| ROT (° C.) | 520° C. | 490° C. | 490° C. |
| H2 | 0.4 | 0.4 | 0.4 |
| C1 | 1.3 | 0.8 | 1.1 |
| C2 | 1.1 | 0.7 | 1.0 |
| C2= | 1.0 | 0.5 | 0.7 |
| Dry gases | 3.9 | 2.5 | 3.3 |
| C3 | 0.9 | 0.7 | 1.0 |
| C3= | 3.7 | 2.0 | 3.4 |
| iC4 | 1.4 | 0.9 | 1.4 |
| nC4 | 0.5 | 0.4 | 0.5 |
| C4=1 | 1.1 | 0.6 | 0.8 |
| iC4= | 1.6 | 1.0 | 1.5 |
| C4=$^2$ | 3.4 | 1.9 | 2.3 |
| LPG | 11.0 | 6.6 | 9.9 |
| LCN (Pi-150° C.) | 35.0 | 24.0 | 18.4 |
| HCN (150-220° C.) | 14.0 | 13.5 | 15.9 |
| TCN (Pi-220° C.) | 49.0 | 37.5 | 34.3 |
| LCO (220-350° C.) | 18.3 | 23.5 | 26.6 |
| Distillate (150-350° C.) | 32.3 | 36.9 | 42.5 |
| Slurry (350+) | 9.9 | 23.0 | 17.7 |
| Coke | 8.0 | 6.9 | 8.1 |

In this Table III, the first column (case 1) demonstrates the yield structure obtained in petrol mode for a reaction temperature of 520° C. and a ratio catalyst over fresh feed of 6.

The second column (case 2) illustrates the yield structure in distillate mode obtained by adapting the operating conditions, mainly the reaction temperature (reduction from 520° C. to 490° C.), which makes it possible to increase the production of distillate (HCN/heavy petrol+LCO/distillate cut) but results in a loss of LPG and an increase in the slurry fractions (HCO/350-440° C.+DCO/440° C.+). However, the production of coke is also reduced, which makes it possible to recycle a portion of the hydrocarbons separated by fractionation to the stripper.

The last column (case 3) illustrates the yield structure after recycling to the stripper 60% of the heart petrol (100-150° C.) produced in the main reactor and 50% of the HCO (350-440° C.) also produced in the main reactor, the petrol being injected into the first cracking zone after the preliminary stripping of the particles separated in the disengager and the HCO being injected into the second cracking zone after stripping of the catalyst particles from the first cracking zone: these two cracking zones are equipped with "packing" as well as the stripping zones, including in the last zone before recycling the catalyst into the regenerator. Under these combined cracking conditions, in the main reactor and in the two cracking zones arranged in the stripper part of the disengager/stripper, the amounts recycled make it possible to increase the production of LPG up to a volume close to that of the petrol mode (case 1) while halving the amount of light petrol and increasing the amount of distillate by 30% compared to the petrol mode. The coke yield is thus maintained relative to that obtained in a petrol mode without imposing additional stress in the regeneration zone. The recycling also makes it possible to reduce by 30% the amount of slurry (350+) produced but does not however make it possible to lower this amount to the production level obtained in petrol mode. Moreover, the slurry yield is lower than the slurry yield obtained in distillate mode without recycle back to the disengager/stripper (case 2).

The invention claimed is:

1. A fluidized-bed catalytic cracking process comprising:
a step of reacting a hydrocarbonaceous feedstock over a fluidized bed of ascending or descending catalyst,
a step of disengaging/stripping coked catalyst particles from cracked effluents, and
a step of regenerating, in one or more stages, the coked catalyst particles, the regenerated catalyst particles recovered at an outlet being sent to an inlet of the fluidized bed of the reaction step,
said process incorporating into the disengaging/stripping step a multi-staged process for cracking and stripping a fluidized mixture of hydrocarbons and of coked catalyst particles, said multi-staged process comprising at least two steps of cracking and one step of stripping after separation of the coked catalyst particles and of cracked effluents, wherein:
said fluidized-bed catalytic cracking process is operating in a mode for maximizing distillates,
said at least two steps of cracking are carried on at least one hydrocarbonaceous fluid over the separated coked catalyst particles followed by said at least one step of stripping these particles, each cracking step preceding a stripping step,
injected into the first cracking step is at least one hydrocarbon chosen from petrol produced or fluid having a boiling point less than or equal to 220° C., and
injected into the second cracking step are products having a boiling point of 350° C. or higher, of HCO type or slurry, recovered at a hydrocarbon fractionating step of the fluidized-bed catalytic cracking process, said first and second cracking steps being separated by a stripping step.

2. Process according to claim 1, characterized in that at least one hydrocarbonaceous fluid is injected over the coked catalyst particles by means of injectors during each cracking step of the multi-staged cracking and stripping process, whilst the coked catalyst particles are stripped during each stripping step of the multi-staged cracking and stripping process, by a stripping fluid, injected countercurrently to the catalyst particles used in the preceding step.

3. Process according to claim 1, characterized in that it comprises, upstream of the first cracking step of the multi-staged cracking and stripping process, a step of pre-stripping the catalyst that consists in countercurrently flushing the stream of coked catalyst particles, resulting from the separation step, with a stripping fluid injected countercurrently to said stream.

4. Process according to claim 1, characterized in that the particles are divided in the various cracking and optionally stripping steps of the multi-staged cracking and stripping process by means of at least one structured packing element.

5. Process according to claim 1, characterized in that two cracking steps are inserted between two stripping steps of the multi-staged cracking and stripping process.

6. Process according to claim 1, characterized in that the stripping steps of the multi-staged cracking and stripping process comprise an injection of gas constituted predominantly of steam and the cracking steps of the multi-staged cracking and stripping process comprise an injection of a recycled hydrocarbonaceous fraction containing less than 5% steam.

7. Process according to claim 1, characterized in that the cracking steps of the multi-staged cracking and stripping process comprise an injection of at least one recycle of hydrocarbons comprising produced petrol or any fluid having a boiling point less than or equal to 220° C. and/or products of HCO type or slurries, recovered at the hydrocarbon fractionating step of the fluidized-bed catalytic cracking process and/or products resulting from other refinery units.

8. Process according to claim 7, characterized in that the hydrocarbons for the recycle may be chosen from $C_6$ and $C_7$ olefins and oligomers having a boiling point of less than 220° C. resulting from the polymerisation of $C_2$ to $C_5$ olefins.

9. Process according to claim 7, wherein said other refinery units are hydrocracking units, biomass units and/or paraffin feedstock units.

10. Process according to claim 1, characterized in that hydrocarbons of the same nature are injected into different cracking steps of the multi-staged cracking and stripping process or hydrocarbons of different nature are injected at each of the cracking steps of the multi-staged cracking and stripping process or else hydrocarbons of different nature are injected jointly into one and the same compartment of one and the same cracking step of the multi-staged cracking and stripping process.

11. Process according to claim 1, characterized in that it comprises a sequence of cracking and stripping steps of the multi-staged cracking and stripping process, comprising an initial pre-stripping step.

12. Process according to claim 11, characterized in that the cracking and stripping steps are inserted between one another, the first step always being a cracking phase, optionally preceded by an initial pre-stripping step, the last being a stripping phase.

13. Process according to claim 1, characterized in that the catalyst used is composed of a conventional catalyst containing up to 15% by weight of at least one additive that promotes the cracking to olefins.

14. Process according to claim 13, wherein said at least one additive is based on ZSM5.

15. Process according to claim 1, carried out using a fluidized-bed catalytic cracking unit comprising a disengager/stripper vessel positioned downstream of a main reactor containing the fluidized bed, said vessel comprising a disengager for the centrifugal and/or ballistic separation of the catalyst particles and of hydrocarbons resulting from the cracking reaction, and a stripper for stripping the catalyst particles which is positioned upstream of the outlet of the catalyst, characterized in that the stripper comprises at least four compartments, at least two cracking compartments and at least two stripping compartments, each comprising, at their base, at least one means of injecting gaseous fluids, optionally equipped with structured packing elements, these elements occupying all or some of the cross section of said compartment.

16. Process according to claim 15, characterized in that the stripper comprises at least one pre-stripping compartment for pre-stripping the catalyst particles that is located upstream of the first cracking compartment, and is equipped with at least one means of injecting a stripping fluid, and optionally with at least one structured or non-structured packing element.

17. Process according to claim 15, characterized in that the stripper comprises a plurality of intercalated cracking and stripping compartments, equipped with at least one means of injecting gaseous fluids, the volumes of all of the cracking and stripping compartments corresponding respectively to 25 to 65% and 35 to 75% of the volume of the stripping zone.

18. Process according to claim 16, characterized in that the pre-stripping compartment occupies up to 25% of the total stripping volume.

\* \* \* \* \*